(12) United States Patent
Tiede

(10) Patent No.: US 11,185,258 B2
(45) Date of Patent: Nov. 30, 2021

(54) HEARING TEST METHOD AND DEVICE

(71) Applicant: Hear Well Be Well Inc., Huntsville (CA)

(72) Inventor: John Edwin Tiede, Huntsville (CA)

( * ) Notice: Subject to any disclaimer, the term of this patent is extended or adjusted under 35 U.S.C. 154(b) by 0 days.

(21) Appl. No.: 17/281,821

(22) PCT Filed: Nov. 8, 2019

(86) PCT No.: PCT/CA2019/000155
§ 371 (c)(1),
(2) Date: Mar. 31, 2021

(87) PCT Pub. No.: WO2020/093135
PCT Pub. Date: May 14, 2020

(65) Prior Publication Data
US 2021/0307655 A1 Oct. 7, 2021

Related U.S. Application Data

(60) Provisional application No. 62/757,839, filed on Nov. 9, 2018.

(51) Int. Cl.
*A61B 5/12* (2006.01)
*A61B 5/15* (2006.01)

(52) U.S. Cl.
CPC ........ *A61B 5/123* (2013.01); *A61B 5/150809* (2013.01); *A61B 2560/04* (2013.01)

(58) Field of Classification Search
CPC .............. A61B 5/123; A61B 5/150809; A61B 2560/04
See application file for complete search history.

(56) References Cited

U.S. PATENT DOCUMENTS

| 6,146,146 | A | 11/2000 | Koby-Olson |
| 2015/0272485 | A1 | 10/2015 | Navat et al. |
| 2017/0047059 | A1* | 2/2017 | Yang ............... A61B 5/123 |

FOREIGN PATENT DOCUMENTS

| DE | 2349626 C2 | 10/1975 |
| EP | 1488618 B1 | 11/2011 |
| WO | 2006/007632 A1 | 1/2006 |

OTHER PUBLICATIONS

PCT/CA2019/000155, International Search Report and Written Opinion of the International Searching Authority, dated Jan. 8, 2020, 7 pgs.

(Continued)

*Primary Examiner* — Sean P Dougherty
(74) *Attorney, Agent, or Firm* — Kagan Binder PLLC

(57) ABSTRACT

A method and device for self-testing a user's hearing. The disposable hearing test device includes a cardboard box containing a sound card with a sound processor, a speaker, and a battery. The sound processor includes a memory containing a digital audio rendition of each of N (e.g. 10) words, and N pressure-activated word buttons. The box has N word pressure regions, each of which when pressed activates a corresponding word button and causes the sound processor to play an audio version of one of the words. The user activates the battery and presses each of the pressure regions in turn, causing the words to be played at a predetermined volume via the speaker. The user then counts the number of correctly recognized words and if the number is less than a threshold, the user is informed of a possible hearing problem.

22 Claims, 2 Drawing Sheets

(56) References Cited

OTHER PUBLICATIONS

J.M. Choi, J. Sohn, Y. Ku, D. Kim and J. Lee, "Phoneme-Based Self Hearing Assessment on a Smartphone," in IEEE Journal of Biomedical and Health Informatics, vol. 17, No. 3, pp. 526-529, May 2013. doi: 10.1109/JBHI.2013.2238549 URL: http://ieeexplore.ieee.org/stamp/stamp.jsp?tp=&arnumber=6407607&isnumber=6511984.

* cited by examiner

HEARING TEST METHOD AND DEVICE

PRIORITY CLAIM

This application claims benefit from International Application No. PCT/CA2019/000155, filed Nov. 8, 2019, which claims the benefit of U.S. Provisional Patent Application No. 62/757,839, filed Nov. 9, 2018, both of which are incorporated herein by reference in their entireties for all purposes.

FIELD OF THE INVENTION

The present invention relates generally to devices and methods for testing a person's hearing, and more particularly to disposable, low-cost hearing self-test devices and methods of using such devices.

BACKGROUND

Word recognition tests are used to assess a person's hearing. A device plays a sequence of words to the person, and after each word is played the person indicates what word he or she thought was played. If the person fails to identify a certain number of the words correctly, that provides an indication that the person may have a hearing problem. Such tests are generally administered by audiologists using specialized equipment or a specially configured computer system. However, this requires that the person schedule, attend and pay for a test session, and requires the use of relatively expensive equipment.

SUMMARY OF THE INVENTION

The invention provides a method of self-testing a user's hearing. The method employs a set of N words, N being an integer greater than 2. The method also employs a predefined volume level for playing the words to the user, where the volume level is selected so that a user with normal hearing would be able to recognize at least M of the N words played through a speaker at the volume level, M being an integer less than N.

The method employs a disposable hearing test device, which includes a sound processor, a speaker, a battery, a sound card, and a box, preferably made from cardboard. In some embodiments, the box may be made from flexible plastic.

The sound processor includes a memory containing a digital audio rendition of each of the N words. N pressure-activated word buttons electronically connected to the sound processor correspond to the N words.

The speaker is electronically connected to the sound processor;

The battery is activatable by the user to supply power to the sound processor and the speaker.

The sound card is connected to the battery and the sound processor.

The cardboard box has front and back panels. The box contains the sound card, the battery, the speaker and the pressure-activated buttons. The front panel includes N word pressure regions, each word pressure region being located proximate to one of the N pressure-activated word buttons. The box has the N words printed (or otherwise indicated) on it so that (a) the words are not visible to the user as the user initially presses the word pressure regions and (b) the printed words are exposable to the user by the user executing an exposure action so that the user can then read the words.

When the battery is activated by the user and the user then presses one of the word pressure regions, the corresponding pressure-activated word button is activated and electronically notifies the sound processor as to which of the pressure-activated word buttons was pressed. When the sound processor receives a notification that a particular pressure-activated word button was pressed, the sound processor retrieves the digital audio rendition of the word corresponding to the particular pressure-activated word button, and causes the speaker to play the digital audio rendition at the sound volume.

The sound card is preferably a printed circuit board (PCB) having the battery and the sound processor mounted thereon.

The method further includes the following steps: activating, by the user, the battery; in turn, pressing, by the user, each of the N word pressure regions and, for each word played by the sound processor, recording the word as understood by the user; performing, by the user, the exposure action to expose the N printed words; counting the number of words that were correctly recognized by the user; and if the number of words that were correctly recognized by the user is less than M, providing an indication to the user that the user has a possible hearing problem.

N may be 10 and M may be 8, for example.

The front panel of the box further may also include L language selection pressure regions, where L is an integer greater than 1, each integer from 1 to L corresponding to a language. In such embodiments, the memory of the sound processor includes L sets of digital audio renditions of each of the N words where the i'th set of digital audio renditions, i being an integer in the range of 1 to L, contains digital audio renditions of the words spoken in the i'th language. Each language selection pressure region is located proximate to one of L pressure-activated language selection buttons in the sound card, so that when the user presses one of the language selection pressure regions corresponding to a particular language, then when the user subsequently presses one of the word pressure regions, the sound processor causes the speaker to play the digital audio rendition of the word corresponding to the pressed word pressure region in the language corresponding to the pressed language selection pressure region. In such embodiments, the method further includes the step of the user pressing one of the L language selection pressure regions to select a language before pressing each of the N word pressure regions. In some embodiments L may be 2 and the languages may be English and French.

The N words are preferably phonetically balanced words containing a balance of high and low frequencies.

All vowels and consonants are preferably included in the N words.

The exposure action may require the user to remove a tab on the front panel of the box to expose printed versions of the N words on the front panel. Alternatively, if the words are printed on the back panel, the exposure action may be for the user to turn the box around so that the back panel is visible to the user.

The indication to the user that the user has a possible hearing problem may be an instruction printed on the front panel of the box that the user should schedule a hearing test if the user correctly identified fewer than M words.

An additional button may be included to allow the user to vary the volume at which the words are played, and the value of M may be a function of the adjusted volume level.

The invention also provides a hearing self-test device including a sound processor as described above, a speaker, a user-activatable battery, a sound card as described above, and a box containing the sound card, the battery, the speaker, and N pressure-activated buttons. The front panel of the box includes N word pressure regions, each word pressure region being located proximate to one of the N pressure-activated word buttons. The box has the N words printed thereon so that (a) the words are not visible to the user as the user initially presses the word pressure regions and (b) the words are exposable to the user by the user executing an exposure action. When the battery is activated and the user then presses one of the word pressure regions, the corresponding pressure-activated word button is activated and electronically notifies the sound processor as to which of the pressure-activated word buttons was pressed. When the sound processor receives a notification that a particular pressure-activated word button was pressed, the sound processor retrieves the digital audio rendition of the word corresponding to the particular pressure-activated word button, and causes the speaker to play the digital audio rendition at a pre-determined sound volume. The pre-determined sound volume is selected so that a user with normal hearing would be able to recognize at least M of the N words played through the speaker at the volume level, M being an integer less than N. The box may be made from cardboard, which may be coated, or from flexible plastic.

DETAILED DESCRIPTION OF THE INVENTION

Figure 1:
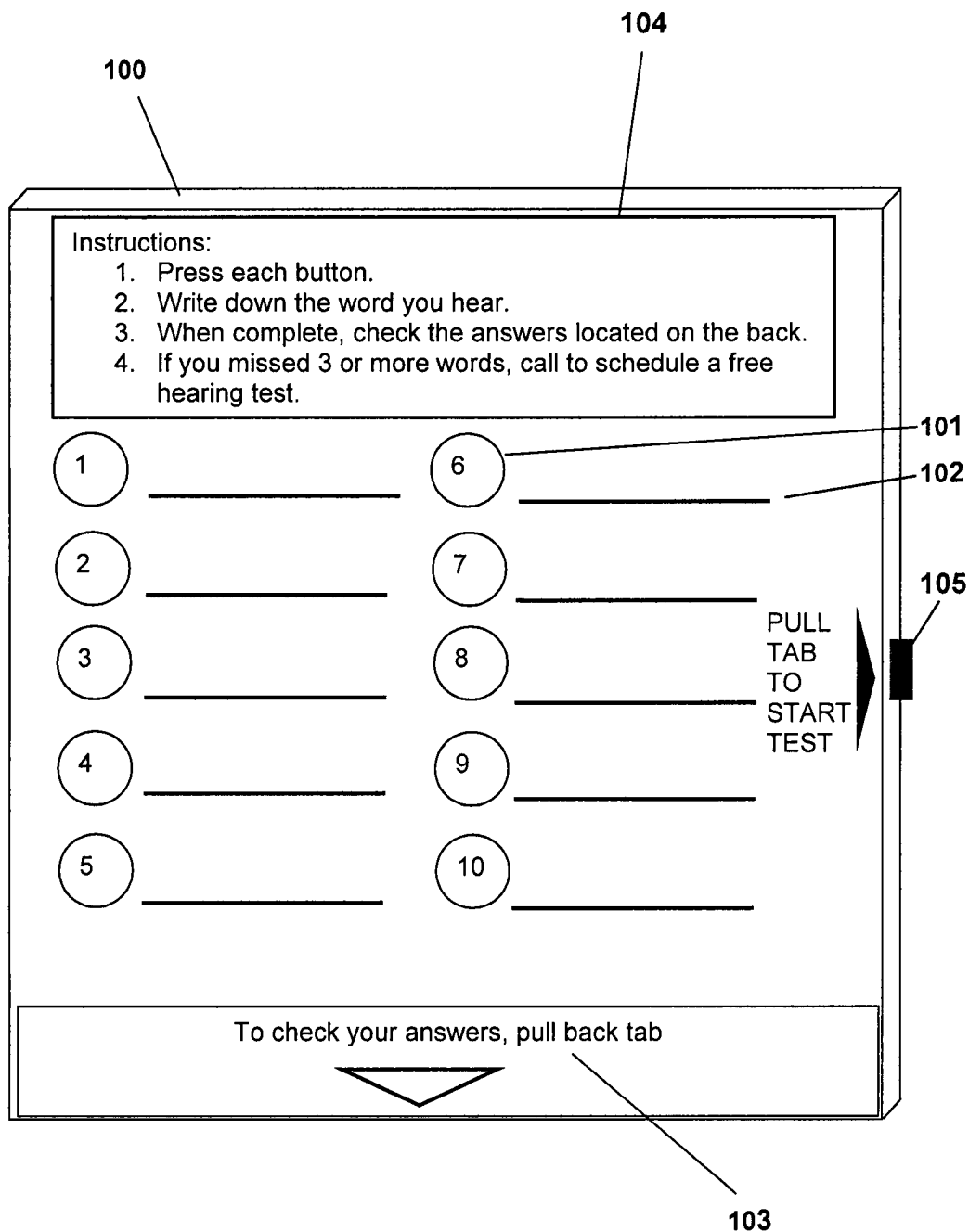
FIG. 1 depicts an embodiment of a hearing test box showing the front panel containing ten word pressure regions.
Figure 2:
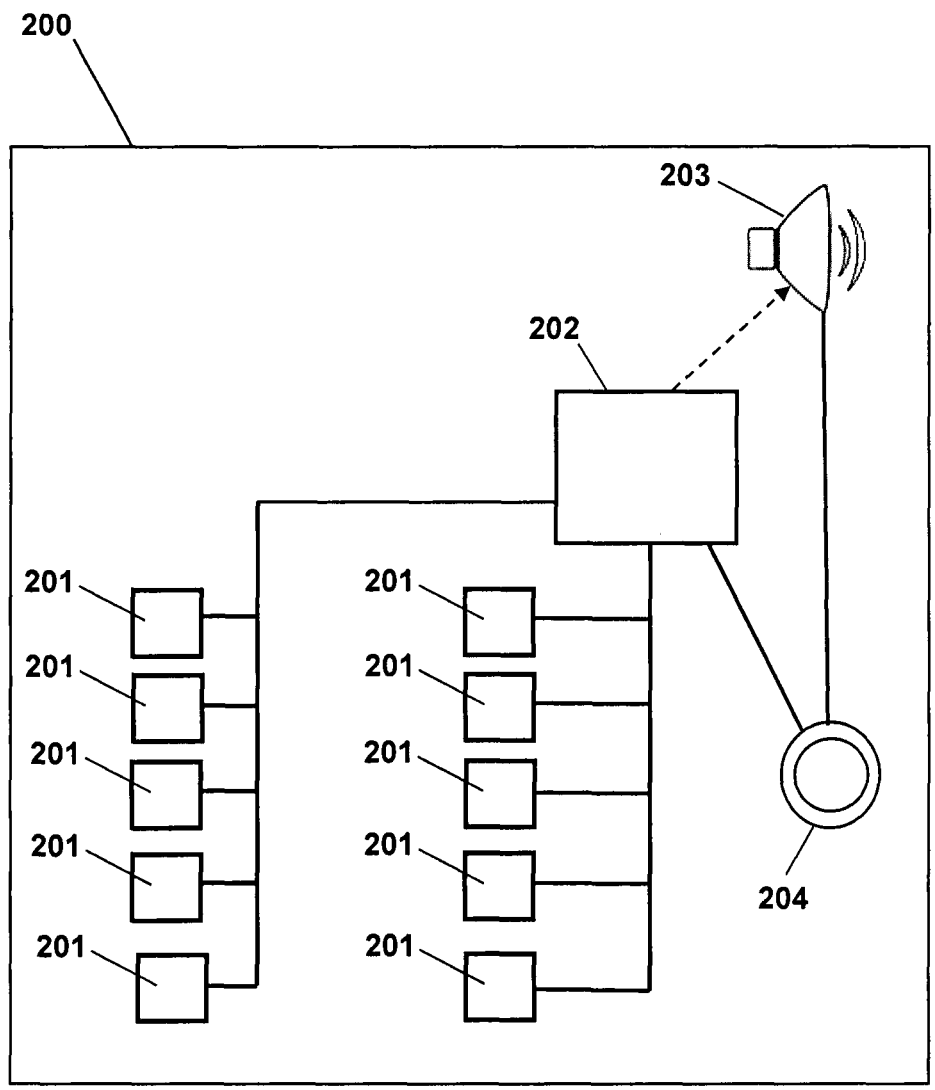
FIG. 2 depicts an embodiment of a sound card, which is a small PCB board, which may be enclosed in the hearing test box, showing the key elements mounted on the sound card.

One embodiment of the invention is shown in FIG. 1. The hearing test device, which may be referred to as a "card", as shown in FIG. 1 includes a box 100 with a relatively small depth, preferably made of a low-cost flexible material, such as coated cardboard/paper or flexible plastic such as polypropylene, or a combination of such low-cost flexible materials. The device is designed to be disposable based on the use of low-cost materials, such as cardboard.

In a battery of hearing tests, words play a significant role in determining someone's ability to hear key frequencies that represent vowels and consonants. In initial clinical testing, using words not only helps a practitioner know the degree of difficulty the patient is experiencing but it helps the patient recognize their own inability to hear all parts of speech. This in turn raises the issues of not being able to follow conversations of family and friends directly back to the patient. People with hearing loss often don't recognize their own problem because the loss is usually gradual over many years, so day to day there is no noticeable change and hearing loss is not recognized. Since this happens gradually, the patient often believes that people mumble, are soft spoken, or that the circumstances are the issue, not them.

Early detection is the key to proper brain health since we hear in our brain. There are many studies indicating a connection with hearing loss and dementia and Alzheimer's and the benefit of wearing hearing aids to reduce the risk.

The present self-test device and method are intended to help individuals recognize if their hearing is below normal parameters and if it requires further assessment by a professional. Presentation of the words may be done, for example, at a preset volume of 65 dB sound pressure level, which enables the subject to pass the word test if the subjects hearing falls within normal limits. If the subject has normal low frequency hearing and a mild to moderate high frequency hearing loss or early onset hearing loss, this self-test will help identify this. Not only can this test be used by the general public, it can also be used by individuals wearing hearing aids.

In a clinic, words are also used in verification of the hearing aid efficacy.

The present self-test can help those wearing hearing aids determine if the hearing aids they wear are still offering them the degree of benefit they received in their initial fitting and will help them recognize that their hearing aids need to be reprogrammed by their professional if they fail to hear the words correctly. The sound card offers a low cost and effective way to screen for hearing loss.

The present method and device addresses problems with the prior art. In particular, the device allows a user to self-test, without needing to schedule, attend and pay for an appointment with an audiologist. The device is designed to be low-cost so that after a user uses the device to test his or her hearing, the user can simply dispose of the device. Such low cost is accomplished by using low-cost, disposable components such as a cardboard box for containing the sound card, and a low-power, non-replaceable battery that is activatable by the user, and after activation provides enough power for the user to perform the self-test.

A concern with disposable devices in particular is whether the device may end up in a landfill. The present device is preferably designed to be fully recyclable. For example the battery is preferably inert and not harmful to the environment, and the box is made from cardboard/paper that can be disposed of in the standard waste and is degradable or can be recycled in the recycling bin. The circuit board and speaker can be recycled at local electronic stores such as Staples's or Best Buy. For embodiments with a battery life of 300 uses, for example, the device can be reused and redistributed in places where there are high density senior communities and residences. This makes the sound card hearing test a very cost effective self-test.

In the depicted embodiment, the device includes a sound card 200, a battery 204, ten pressure-activated word buttons 201, a sound integrated circuit (IC) chip 202 (or "sound processor"), and a speaker 203. The sound card 200 is a small printed circuit board (PCB). The battery and sound processor are attached to the PCB and electronically connected to each other by the PCB. In this sound card, digital audio versions of words are stored and can be played by the sound processor via the speaker 203. The total sound time may be, for example, 34 seconds for a particular embodiment. The sound time can be customized to be longer or shorter.

Preferably the battery 204 is a low-cost battery (which may comprise multiple low-cost batteries) that provides sufficient power to play each of the words at least once, and preferably more than once, for example in some embodiments, up to 300 times. For example, the battery 204 may include three AG13/LR44 batteries located in three battery holders that are connected to the PCB.

The sound processor may be programmed by software contained in a memory accessible by the processor, or may be hard-wired to perform the functions described herein.

The speaker size may be, for example, 29 mm, 8Ω, 0.25 W. The speaker may be attached the box 100. The speaker 203 is electronically connected to the sound card (e.g. via wires) to obtain power from the battery 204, if required, and to receive sound to be played from the sound processor. The speaker 203 may be fully enclosed in the box 100, in which case the sound then passes through the front panel, which is relatively thin. The box 100 may include an opening proximate to the speaker 203 to better facilitate the user hearing the words played via the speaker 203, but this is generally not preferred. The pre-determined volume at which the words are played means the volume as heard by a user proximate to the card, which may depend on the location of the speaker 203 and the sound path (e.g. through the front panel, and/or via one or more openings in the box 100) between the speaker 203 and the user, when the user is facing the front panel and holding the box 100.

In an embodiment of the sound card 200, each word may be about three seconds, with 10 words totaling about 34 seconds.

The battery is preferably activatable by the user, for example by the user pulling out a tab 105. The battery preferably supports replay of the words, for example, up to 300 times. The battery is not replaceable, and is sealed, along with the sound processor, speaker and the pressure-activated word buttons inside the box.

The pressure-activated word buttons are electronically connected to the sound processor, for example by wires.

The sound card 200 and box are typically made to a custom size to suit the needs of a particular provider.

The box may have outer panels made from cardboard, or coated cardboard, and also comprise inside the box a stiff material, such as a foam material, that secures the sound card, speaker and pressure-activated word buttons inside the box in a fixed location relative to the outer panels of the box. In other embodiments, the sound card, speaker and pressure-activated word buttons may be otherwise secured inside the box to fix their positions.

Additional buttons may be employed to select more than one language. Such a device may have for example, 13 buttons, 10 buttons of which are used to play 10 words, and the other three buttons are used to select the language. For example, when the user presses button 1, the words are spoken in English, so that when one of the 10 word buttons is pressed, the card will play the word corresponding to that button in English. When button 2 is pressed, then the words may be played in French, or if button 3 is pressed, the words may be played in Spanish. Multiple languages can be added to the card. The language selection buttons may, for example, be placed above the ten word list across the top. Five or more languages may be support by one card by adding additional buttons.

The sound card 200 is designed to help individuals determine if they have any hearing loss. This is a self-test that can be done anywhere and for best results should be taken in a quiet environment. Natural conversation levels are typically between 45 and 55 dB HL or 65 to 75 dB SPL and the sound card can be designed to specific target groups.

Another button that can change the volume to specific levels may also be employed. Having multiple volume levels, the device can be used to determine the severity of the hearing loss. As an example having three volume levels can help the tester determine at what level they can hear more or fewer words. Level one can be set to a soft voice and the user with normal hearing will pass the test. If the user has a slight or mild hearing loss they will miss three or more words and prompt them to schedule a hearing test. At volume level 2, those with normal and mild hearing loss will pass the test and the subject with mild to moderate hearing loss will miss three or more words and will call to schedule a hearing test. At the third level of volume, only individuals with greater than a moderate loss will call for a hearing test.

By having a fixed volume level the outcomes and call to action can easily be changed by setting the number of pass and fail word number when the test is performed. As an example, if a fixed volume of 70 dB is used then the call to action may be three or more words missed. By using three words missed as a call to action individuals with a slight loss will pass since they will get 10 out of 10 words correct. If they have a mild hearing loss they will miss one to three words and only some of them will call to schedule a hearing test. If they have a mild to moderate or moderate or more severe hearing loss the score will be worse than three and they will call to get a hearing test. To limit the number of mild hearing loss individuals calling for a hearing test the call to action score may be changed to missing four out of 10, or five out of 10. As the hearing loss in the card user becomes worse, the number of words missed will increase. This is typically mild to moderate, moderate to moderately severe or greater.

Individuals with a slight or mild hearing loss can benefit from hearing aids, but may not be experiencing enough difficulty to warrant a purchase of hearing aids.

The words used for the test are preferably phonetically balanced words. These words contain a balance of high and low frequencies. Preferably, all vowels and consonants are specifically used because the test is designed to determine if all vowels and consonants can be heard in a word. This is much like trying to see individual letters during an eye exam.

With hearing loss, whether age related or noise induced, high frequencies tend to deteriorate more often than low frequencies. This can lead to not hearing clearly and words sounding mumbled. Low frequencies become dominant so when hearing the word "stiff", for example, it could sound like "sit". "Dust" may sound like "duck". A heavier weighting on low frequency vowels is prevalent in such an individual's hearing.

When all frequencies are about the same in thresholds across all the speech frequencies, this may lead to not hearing things loud enough as well as not clearly enough. The score on this self-test is preferably configured to indicate a higher number of missed words out of ten.

This is an easy to use hearing test. To begin, the user opens the card and pulls the tab 105 on the side to activate the battery.

The test should be performed in a quiet environment.

If a choice of language is present, the user first presses one of the language buttons before pressing the word buttons.

Then, the user presses a word pressure region 101 and writes down the word the user heard on a line 102 beside the button/pressure region. Other means of recording the user's understanding of the word may alternatively be employed. For example, the user may write the words as understood on a piece of paper. A kit may be provided including the device and multiple pre-printed sheets of paper with numbers correspond to the N words, and a designated place (e.g. a line) for each number in which the user can record the word as understood by the user.

The pressure regions 101 may be circular, as depicted, but other shapes such as squares are possible. The word number may be placed inside each pressure region 101 as depicted, or alternatively it may be otherwise placed proximate to the pressure region 101, such as beside the pressure region 101. Each pressure region 101 corresponds to one pressure-activated button 201 on the PCB board 200 and is configured so that when the user presses the pressure region 101, then the corresponding pressure-activated button 201 is activated, thereby signaling the sound processor 202 as to which button was pressed. The sound processor 202 then retrieves stored digital audio from a memory and causes the audio to be played via the speaker 203, so that the user can hear the word at the pre-defined volume level. The stored audio is a digital audio rendition of the word corresponding to the particular pressure-activated button. This may derive from a person speaking the word into a speaker connected to a processor which has an analogue to digital converter which digitizes the sound to produce a digital audio clip/file, which may be stored, for example in WAV, FLAG, MP3 or Vorbis format.

After pressing all 10 pressure regions and hearing all ten words, and recording all ten words as understood by the user, the user checks his or her answers on the back of the card, or elsewhere on the card, and scores the test. The user must execute an exposure action to expose the printed words after the user has listened to the words and attempted to recognize them. In some embodiments, the exposure action user may be pulling a tab as indicated in item 103 in FIG. 1 in order to reveal the correct answers that are written on the front panel of the box under the tab 103. In other embodiments, the words may be printed on the back panel of the box 100, and the exposure action is then turning the box 100 around to see the printed words. If this case, the words may be printed upside-down in order to reduce the risk of the user inadvertently seeing the words before taking the test.

If the user misses a threshold number of words, which is typically three words or more words out of ten, then the user is advised 104 to call a hearing professional to have the user's hearing checked for hearing loss.

As well as home use, the hearing test device can also be used by family physicians to help identify hearing loss in the examination room easily by playing the ten words and assessing the response by the patient.

In retirement homes and nursing homes the hearing test device can be used as a simple screener when admitting new residents for example.

In schools, the hearing test device may be used to determine if a student is having difficulty hearing clearly.

There are hundreds of phonetically balanced words to choose from that come in multiple languages.

The use of exactly 10 pressure regions, pressure-activated buttons, and stored digital words is not essential. For example, embodiments with 8, 12, 15 and 20 of each are possible. The use of 10 words is considered to be a reasonable trade-off between effectiveness and complexity/cost.

The sound processor 202 is a computing device that preferably comprises a single integrated circuit chip with sufficient non-volatile memory to store the digital audio renditions for the number of words the card is configured to play. The non-volatile memory may be integral to the chip, or be one or more separate memory chips.

It is preferred that the battery be selected to support one instance of the device being used by multiple people. For example, a first user may take the test, and then pass the device on to a friend or family member. In such embodiments it is preferred that the user record the user's understanding of the words played on a separate medium from the device, and also that the printed words are on the back panel of the device rather than on the front panel where they are exposable by pulling a tab, as in FIG. 1, or otherwise exposable so that a subsequent user would not see the words when pressing the word pressure regions.

The device may also have a front cover that connects to the back panel of the box and is foldable to cover the front panel when closed, and can be opened to expose the front panel to the user.

Generally, a computer, computer system, computing device, client or server, as will be well understood by a person skilled in the art, includes one or more than one electronic computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. It is the express intent of the inventors that a "processor" does not include a human; rather it is limited to be an electronic device, or devices, that perform digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.) Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed. Unless expressly stated or otherwise clearly implied herein, the conjunction "or" as used in the specification and claims shall be interpreted as a non-exclusive "or" so that "X or Y" is true when X is true, when Y is true, and when both X and Y are true, and "X or Y" is false only when both X and Y are false.

The words "comprises" and "comprising", when used in this specification and the claims, are used to specify the presence of stated features, elements, integers, steps or components, and do not preclude, nor imply the necessity for, the presence or addition of one or more other features, elements, integers, steps, components or groups thereof.

It should be understood that the above-described embodiments of the present invention, particularly, any "preferred" embodiments, are only examples of implementations, merely set forth for a clear understanding of the principles of the invention. Many variations and modifications may be made to the above-described embodiment(s) of the invention as will be evident to those skilled in the art. That is, persons skilled in the art will appreciate and understand that such modifications and variations are, or will be, possible to utilize and carry out the teachings of the invention described herein.

The scope of the claims that follow is not limited by the embodiments set forth in the description. The claims should be given the broadest purposive construction consistent with the description and figures as a whole.

What is claimed is:

1. A method of self-testing a user's hearing comprising the steps of:
   providing a set of N words, N being an integer greater than 2;
   providing a volume level for playing the words to the user, the volume level having been selected so that a user with normal hearing would be able to recognize at least M of the N words played through a speaker at the volume level, M being an integer less than N;
   providing a disposable hearing test device comprising:
      a sound processor comprising a memory containing a digital audio rendition of each of the N words corresponding to N pressure-activated word buttons that are electronically connected to the sound processor;
      the speaker, the speaker being electronically connected to the sound processor;
      a battery that is activatable by the user to supply power to the sound processor;
      a sound card electronically connected to the battery and the sound processor;
      the N pressure-activated word buttons; and
      a box having front and back panels, the box containing the sound card, the battery, the speaker and the pressure-activated word buttons, the front panel comprising N word pressure regions, each word pressure region being located proximate to one of the N pressure-activated word buttons, the box having the N words printed thereon so that (a) the words are not visible to the user as the user initially presses the word pressure regions and (b) the printed words are exposable to the user by the user executing an exposure action; and
   wherein when the battery is activated by the user and the user presses one of the word pressure regions, the corresponding pressure-activated word button is activated and electronically notifies the sound processor as to which of the pressure-activated word buttons was pressed,
   wherein when the sound processor receives a notification that a particular pressure-activated word button was pressed, the sound processor retrieves the digital audio rendition of the word corresponding to the particular pressure-activated word button, and causes the speaker to play the digital audio rendition at the volume level;
   activating the battery;
   in turn, pressing each of the N word pressure regions and, for each word played by the sound processor, recording the word as understood by the user;
   performing the exposure action to expose the N printed words;
   counting the number of words that were correctly recognized by the user; and
   if the number of words that were correctly recognized by the user is less than M, providing an indication to the user that the user has a possible hearing problem.

2. The hearing test device of claim 1, wherein the box comprises cardboard.

3. The hearing test device of claim 1, wherein the box comprises flexible plastic.

4. The method of claim 1, wherein the sound card is a PCB board having the battery and the sound processor mounted thereon.

5. The method of claim 1, wherein N is 10 and M is 8.

6. The method of claim 1, wherein the front panel of the box further comprises L language selection pressure regions, where L is an integer greater than 1, each integer from 1 to L corresponding to a language, the memory of the sound processor comprising L sets of digital audio renditions of each of the N words where the i'th set of digital audio renditions, i being an integer in the range of 1 to L, contains digital audio renditions of the words spoken in the i'th language, each language selection pressure region being located proximate to one of L pressure-activated language selection buttons in the sound card, so that when the user presses one of the language selection pressure regions corresponding to a particular language, then when the user subsequently presses one of the word pressure regions, the sound processor causes the speaker to play the digital audio rendition of the word corresponding to the pressed word pressure region in the language corresponding to the pressed language selection pressure region, and wherein the user presses one of the L language selection pressure regions to select a language before pressing each of the N word pressure regions.

7. The method of claim 6, wherein L is 2 and the languages are English and French.

8. The method of claim 1, wherein the N words are phonetically balanced words containing a balance of high and low frequencies.

9. The method of claim 1, wherein all vowels and consonants are included in the N words.

10. The method of claim 1, wherein the exposure action comprises removing a tab on the front panel of the box to expose printed versions of the N words on the front panel.

11. The method of claim 1, wherein printed versions of the N words are provided the back panel, and the exposure action comprises turning the box so that the user can view the printed words on the back panel.

12. The method of claim 1, wherein the indication to the user that the user has a possible hearing problem is an instruction printed on the front panel of the box that the user should schedule a hearing test if the user correctly identified fewer than M words.

13. The method of claim 1, wherein an additional button is provided to vary the volume at which the words are played, and the value of M is a function of the adjusted volume level.

14. The method of claim 1, wherein the front panel further comprises N lines, each line being proximate to one of the N word pressure regions, wherein after the user presses one of the word pressure regions, the user records the word as understood by writing the word as understood by the user on the line beside the pressed word pressure region.

15. A disposable hearing self-test device comprising:
a sound processor comprising a memory containing a digital audio rendition of each of N words corresponding to N pressure-activated word buttons electronically connected to the sound processor;
a speaker electronically connected to the sound processor;
a battery that is activatable by a user to supply power to the sound processor,
a sound card having the battery and the sound processor attached and electronically connected thereto;
the N pressure-activated word buttons; and
a box having front and back panels, the box containing the sound card, the battery, the speaker and the pressure-activated word buttons, the front panel comprising N word pressure regions, each word pressure region being located proximate to one of the N pressure-activated word buttons, the box having the N words printed thereon so that (a) the words are not visible to the user as the user initially presses the word pressure regions and (b) the words are exposable to the user by the user executing an exposure action; and
wherein when the battery is activated and the user then presses one of the word pressure regions, the corresponding pressure-activated word button is activated and electronically notifies the sound processor as to which of the pressure-activated word buttons was pressed,
wherein when the sound processor receives a notification that a particular pressure-activated word button was pressed, the sound processor retrieves the digital audio rendition of the word corresponding to the particular pressure-activated word button, and causes the speaker to play the digital audio rendition at a pre-determined sound volume,
wherein the pre-determined sound volume is selected so that a user with normal hearing would be able to recognize at least M of the N words played through the speaker at the pre-determined sound volume, M being an integer less than N.

16. The hearing self-test device of claim 15, wherein the sound card is a printed circuit board having the battery and the sound processor mounted thereon.

17. The hearing self-test device of claim 15, wherein N is 10 and M is 8.

18. The hearing self-test device of claim 15, wherein the panel further comprises L language selection pressure regions, where L is an integer greater than 1, each integer from 1 to L corresponding to a language, the memory of the sound processor comprising L sets of digital audio renditions of each of the N words where the i'th set of digital audio renditions, i being an integer in the range of 1 to L, are digital audio renditions of the words spoken in the i'th language, each language selection pressure region being located proximate to one of L pressure-activated language selection buttons in the sound card, so that when the user presses one of the language selection pressure regions corresponding to a particular language, then when the user subsequently presses one of the word pressure regions, the sound processor causes the speaker to play the digital audio rendition of the word corresponding to the pressed word pressure region in the language corresponding to the pressed language selection pressure region.

19. The hearing self-test device of claim 15, wherein the box comprises cardboard.

20. The hearing self-test device of claim 15, wherein the box comprises flexible plastic.

21. The hearing self-test device of claim 15, wherein the device is fully recyclable, the battery being inert and the box being made from recyclable cardboard or paper.

22. The hearing self-test device of claim 15, wherein the battery is selected to permit a plurality of users to use the device to perform a hearing test.

* * * * *